(12) United States Patent
Sotoyama et al.

(10) Patent No.: US 6,783,872 B2
(45) Date of Patent: Aug. 31, 2004

(54) DINAPHTOPYRENE COMPOUND, AND ORGANIC EL ELEMENT AND ORGANIC EL DISPLAY USING THE SAME

(75) Inventors: Wataru Sotoyama, Kawasaki (JP); Hiroyuki Sato, Kawasaki (JP); Azuma Matsuura, Kawasaki (JP); Toshiaki Narusawa, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 10/108,388

(22) Filed: Mar. 29, 2002

(65) Prior Publication Data

US 2003/0113579 A1 Jun. 19, 2003

(30) Foreign Application Priority Data

Nov. 8, 2001 (JP) ........................................ 2001-342678

(51) Int. Cl.$^7$ .......................... H05B 33/12; C07C 15/20; C07C 211/61

(52) U.S. Cl. ....................... 428/690; 428/917; 313/504; 313/506; 252/301.16; 564/426

(58) Field of Search ................................ 428/690, 917; 313/504, 506; 252/301.16; 564/426

(56) References Cited

FOREIGN PATENT DOCUMENTS

| | | |
|---|---|---|
| EP | 0 866 110 A1 | 9/1998 |
| JP | 5-32596 | 2/1993 |
| JP | 5-190283 | 7/1993 |
| JP | 5-194943 | 8/1993 |
| JP | 6-219973 | 8/1994 |
| JP | 07-110940 | 4/1995 |
| JP | 8-259940 | 10/1996 |
| JP | 10--289786 | 10/1998 |
| JP | 11-87057 | 3/1999 |
| JP | 11-273864 | 10/1999 |
| JP | 2000-26337 | 1/2000 |
| JP | 2001-102172 | 4/2001 |
| JP | 2001-118682 | 4/2001 |

OTHER PUBLICATIONS

ZCA 65:95751 (Original Reference No. 65–17920e–f; Tables of quantum chemical data. IX. Energy characteristics of some benzenoid hydrocarbons, Titz. et al., Collection Czech. Chem. Commun., 31(10), pp. 4168–4172, 1966).*
C. W. Tang and S. A. VanSlyke, "Organic electroluminescent diodes", Applied Physics Letters vol. 51(12), pp. 913–915, Sep. 1987.
C. W. Tang, S. A. VanSlyke, and C. H. Chen, "Electroluminescence of doped organic thin films", Journal of Applied Physics vol. 65(9), pp. 3610–3616, May 1989.
English Abstract of Publication No. 5–222361; Dated Aug. 31, 1993; Inventor: Tashiro Masashi et al.
English Abstract of Publication No. 06–136359; Dated May 17, 1994; Inventor: Nishio Yoshitaka et al.
English Abstract of Publication No. 06–140156; Dated May 20, 1994; Inventor: Nishio Yoshitaka et al.
English Abstract of Publication No. 06–219973; Dated Aug. 9, 1994; Inventor: Nagai Kazukiyo et al.
English Abstract of Publication No. 07–101911; Dated Apr. 18, 1995; Inventor: Tamoto Nozomi et al.
English Abstract of Publication No. 07–282975; Dated Oct. 27, 1995; Inventor: Iwanaga Hideaki et al.
English Abstract of Publication No. 09–188874; Dated Jul. 22, 1997; Inventor: Ebisawa Akira et al.
English Abstract of Publication No. 10–067984; Dated Mar. 10, 1998; Inventor: Takahashi Hisamitsu et al.
English Abstract of Publication No. 10–088122; Dated Apr. 7, 1998; Inventor: Tamura Shinichiro et al.
English Abstract of Publication No. 10–255985; Dated Sep. 25, 1998; Inventor: Shoan She et al.
English Abstract of Publication No. 11–185962; Dated Jul. 9, 1999; Inventor: Kin Reikei et al.
English Abstract of Publication No. 11–199864; Dated Jul. 27, 1999; Inventor: Ri Saigyongu et al.
English Abstract of Publication No. 11–214152; Dated Aug. 6, 1999; Inventor: Yasukawa Koji et al.
English Abstract of Publication No. 11–329719; Dated Nov. 30, 1999; Inventor: Hyon Yun O et al.
English Abstract of Publication No. 11–354283; Dated Dec. 24, 1999; Inventor: Nakamura Hiroaki et al.
English Abstract of Publication No. 2000–136379; Dated May, 16, 2000; Inventor: Noguchi Masanobu et al.

(List continued on next page.)

*Primary Examiner*—Marie Yamnitzky
(74) *Attorney, Agent, or Firm*—Staas & Halsey

(57) ABSTRACT

An organic EL element utilizes a dinaphthopyrene compound that has a high color purity of green light, excellent light-emitting efficiency, light-emitting luminance. The organic EL element has, in between a positive electrode and a negative electrode, an organic thin-film layer including a light-emitting layer. The organic thin-film layer contains the dinaphthopyrene compound comprising a structure expressed by the following structural formula:

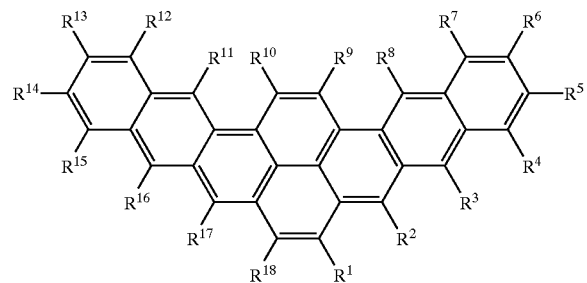

where $R^1$ through $R^{18}$ may be the same or may be different, and represent hydrogen atoms or substituents. At least one of $R^1$ through $R^{18}$ preferably is selected from aryl groups, arylamino groups and diarylamino groups.

28 Claims, 3 Drawing Sheets

OTHER PUBLICATIONS

English Abstract of Publication No. 2000–164363; Dated Jun. 16, 2000; Inventor: Kawamura Hisayuki et al.

English Abstract of Publication No. 2000–212466; Dated Aug. 2, 2000; Inventor: Chun Yup Kim et al.

English Abstract of Publication No. 2000–231987; Dated Aug. 22, 2000; Inventor: Toyama Wataru et al.

English Abstract of Publication No. 2000–243575; Dated Sep. 8, 2000; Inventor: Takayama Koichi et al.

English Abstract of Publication No. 2000–273056; Dated Oct. 3, 2000; Inventor: Hosokawa Chishio et al.

English Abstract of Publication No. 1999–009764/200224; Dated Mar. 19, 2002.

English Abstract of Publication No. 2001–003044; Dated Jan. 9, 2001; Inventor: Matsuo Mikiko et al.

English Abstract of Publication No. 2001–023778; Dated Jan. 26, 2001; Inventor: Kin Reikei et al.

English Abstract of Publication No. 2001–052861; Dated Feb. 23, 2001; Inventor: Fujita Yoshimasa et al.

English Abstract of Publication No. 2001–064529; Dated Mar. 13, 2001; Inventor: Tanaka Tatsuo et al.

English Abstract of Publication No. 2001–089681; Dated Apr. 3, 2001; Inventor: Takiguchi Takao et al.

English Abstract of Publication No. 2001–102174; Dated Apr. 13, 2001; Inventor: Hironaka Yasuo et al.

English Abstract of Publication No. 2001–118682; Dated Apr. 27, 2001; Inventor: Toyama Wataru et al.

English Abstract of Publication No. 2001–126874; Dated May 11, 2001; Inventor: Chondroudis Konstantinos et al.

English Abstract of Publication No. 2001–131541; Dated May 15, 2001; Inventor: Hosokawa Chishio et al.

English Abstract of Publication No. 3046814; Dated Mar. 17, 2000; Inventor: Chun Yup Kim et al.

English Abstract of Publication No. 3099497; Dated Aug. 18, 2000; Inventor: Tashiro Masashi et al.

Becker, Ralph S. et al., "Electron Affinities and Ionization Potentials of Aromatic Hydrocarbons", *Journal of the American Chemical Society*, vol. 85, Aug. 5, 1963, pp. 2210–2214.

* cited by examiner

Schematic View of Passive Matrix Panel

Circuit Diagram of Passive Matrix Panel

Schematic View of Active Matrix Panel

Circuit Diagram of
Active Matrix Panel

DINAPHTOPYRENE COMPOUND, AND ORGANIC EL ELEMENT AND ORGANIC EL DISPLAY USING THE SAME

CROSS-REFERENCE TO RELATED APPLICATIONS

This application is based upon and claims priority of Japanese Patent Application No. 2001-342678, filed Nov. 8, 2001.

BACKGROUND OF THE INVENTION

1. Field of the Invention

The present invention relates to a dinaphthopyrene compound which is suitably used in an organic EL element, an organic EL element using the dinaphthopyrene compound, and an organic EL display using the organic EL element.

2. Description of the Related Art

Organic EL elements have features such as self-lighting, high-speed response, and the like, and application thereof to flat panel displays is expected. Specifically, the EL elements in which a light emitting element having a large surface area which operates at 10V or less, is gathering people's attention specifically after a two layered type. (laminated types) which laminates a positive hole transporting organic thin layer (positive hole transporting layer) and an electron transporting organic thin layer (electron transporting layer) laminated in two layers, have been reported (C. W. Tang and S. A. Van Slyke, Applied Physics Letters vol. 51, 913 (1987)). A laminated type organic EL element may have a basic structure of positive electrode/positive hole transporting layer/light emitting layer/electron transporting layer/negative electrode, and for the light emitting layer, a two layered types as mentioned earlier, the positive hole transporting layer or the electron transporting layer which functions on behalf of the light emitting layer may be used. In order to obtain an organic EL element having a high efficiency of light emission, the light emitting layer needs to have a high efficiency of light emission, and as such, the light emitting layer, excluding those which forms a layer using a single material, may include a type in which a small amount of high fluorescent light emitting pigment molecules are doped in the primary ingredient of a host material (C. W. Tang, S. A. Van Slyke, and C. H. Chen, Journal of Applied Physics vol. 65, 3610 (1989)).

However, with these organic EL elements, there is the problem that the color of the emitted light and the light-emitting efficiency are insufficient in actual use, and further improvements in actual use are required.

SUMMARY OF THE INVENTION

The present invention focuses on addressing these concerns, overcoming the aforementioned drawbacks of the prior art, and achieving the following object. Namely, an object of the present invention is to provide a dinaphthopyrene compound which has high color purity of green light and excellent light-emitting efficiency, light-emitting luminance and the like and which is suitable for an organic EL element, an organic EL element which uses the dinaphthopyrene compound and has high color purity of green light and excellent light-emitting efficiency, light-emitting luminance and the like, and an organic EL display which is high-performance and utilizes the organic EL element.

As a result of intensive studies carried out by the present inventors in order to overcome the above drawbacks, the present inventors discovered the following. Namely, specific dinaphthopyrene compounds have high color purity of green light and excellent light-emitting efficiency, light-emitting luminance and the like, and are particularly suited for organic EL elements which are used for emitting green light. An organic EL element and an organic EL display using this dinaphthopyrene compound have high color purity of green light and excellent light-emitting efficiency, light-emitting luminance and the like, and are high-performance, and can emit light at a higher luminance than conventional structures. Further, the dinaphthopyrene compound has excellent transportability of positive holes (carrier) or electrons. An organic EL element and an organic EL display which use the dinaphthopyrene compound in at least one of a positive hole transporting layer and an electron transporting layer have high color purity of green light and excellent light-emitting efficiency, light-emitting luminance and the like, are high-performance, and can emit light at a higher luminance than conventional structures.

The dinaphthopyrene compound of the present invention is a dinaphthopyrene compound comprising a structure expressed by the following structural formula Structural Formula

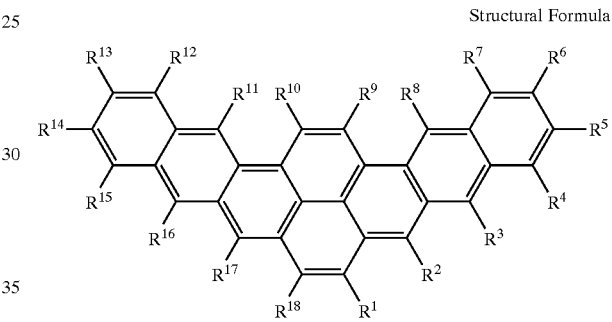

where $R^1$ through $R^{18}$ may be the same or may be different to each other, and represent hydrogen atoms or substituents (excluding cases in which all are hydrogen atoms).

The organic EL element of the present invention is an organic EL element comprising an organic thin-film layer including a light-emitting layer in between a positive electrode and a negative electrode and the organic thin-film layer contains a dinaphthopyrene compound wherein the dinaphthopyrene compound comprising a structure expressed by the following structural formula

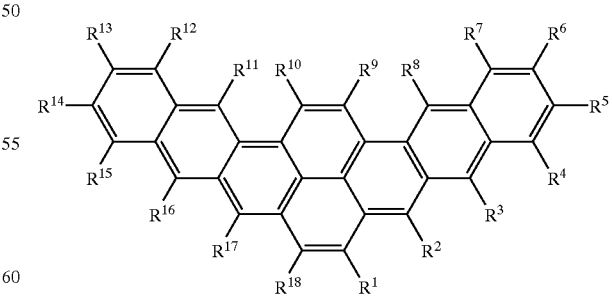

where $R^1$ through $R^{18}$ may be the same or may be different to each other, and represent hydrogen atoms or substituents.

The organic EL display of the present invention uses the organic EL element of the present invention.

DESCRIPTION OF THE PREFERRED EMBODIMENTS

<Dinaphthopyrene Compound>

Figure 1:
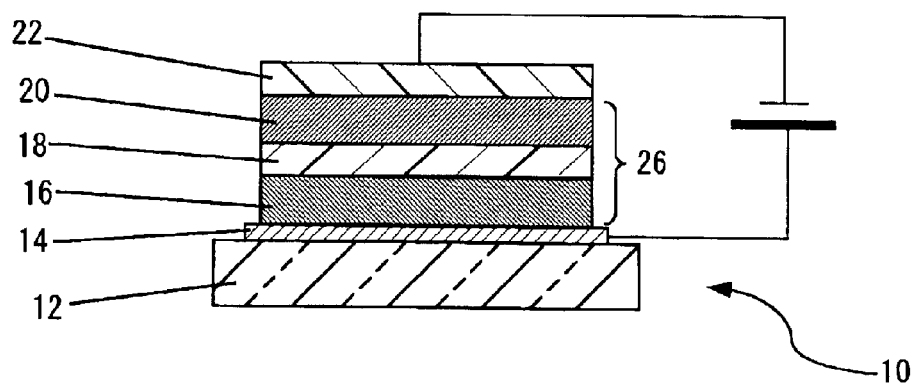
FIG. 1 is a schematic explanatory view for explaining an example of a layer structure in an organic EL element of the present invention.

The dinaphthopyrene compound of the present invention is expressed by the following structural formula.

Structural Formula

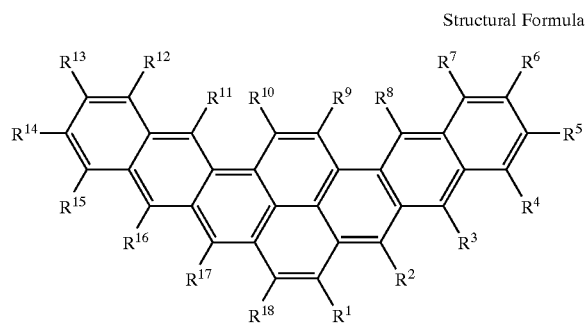

where $R^1$ through $R^{18}$ may be the same or may be different to each other, and represent hydrogen atoms or substituents (excluding cases in which all are hydrogen atoms).

The substituents are not particularly limited provided that the color emission of the dinaphthopyrene compound exhibits green (G) (i.e., provided that the light-emitting wavelength is about 490 to 560 nm), and may be appropriately selected in accordance with the object. It is preferable to select, for example, a halogen atom, a hydroxyl group, a cyano group, an alkyl group, an alkoxyl group, an aryl group, an aryloxy group, an arylamino group, a diarylamino group, or the like.

When the dinaphthopyrene compound has these substituents, the operation and effects of the substituents are as follows.

If the substituents are halogen atoms or alkyl groups, these substituents increase the affinity of the dinaphthopyrene compound and a host compound which will be described later.

If the substituents are hydroxyl groups, cyano groups, alkoxyl groups or aryloxy groups, these substituents shift the color of the emitted light of the dinaphthopyrene compound in the direction of longer wavelengths.

If the substituents are aryl groups, the substituents suppress the concentration quenching due to the association between the molecules, by making the flat mother core of the dinaphthopyrene compound be a stereo structure.

If the substituents are arylamino groups or diarylamino groups, these substituents shift the color of the emitted light of the dinaphthopyrene compound in the direction of longer wavelengths, and improve the positive hole transportability of the dinaphthopyrene compound, and suppress the concentration quenching due to the association between the molecules, by making the flat mother core of the dinaphthopyrene compound be a stereo structure.

Examples of the halogen atom are fluorine, chlorine, bromine, and the like.

The alkyl group is not particularly limited, and can be appropriately selected in accordance with the object. Suitable examples are straight chain, branched or cyclic alkyl groups having from 1 to 10 carbon atoms. Specific suitable examples include methyl, ethyl, propyl, isopropyl, butyl, isobutyl, tertiary butyl, pentyl, isopentyl, hexyl, isohexyl, heptyl, isoheptyl, octyl, isooctyl, nonyl, isononyl, decyl, isodecyl, cyclopentyl, cyclobutyl, cyclopropyl, cyclohexyl, cycloheptyl, cyclooctyl, cyclononyl, cyclodecyl, and the like.

The alkoxy group is expressed by —OR (where R represents the aforementioned alkyl groups). Examples include methoxy, ethoxy, propoxy, isopropoxy, cyclopropoxy, butoxy, isobutoxy, cyclobutoxy, cyclopentoxy, cyclohexyloxy, and the like.

The aryl group is not particularly limited, and can be appropriately selected in accordance with the object. Suitable examples include monocyclic aromatic ring groups, groups formed by four or fewer aromatic rings being bonded together, groups having five or fewer condensed aromatic rings and whose total number of carbon, oxygen, nitrogen, and sulfur atoms is 30 or less, and the like.

The monocyclic aromatic ring group is not particularly limited, and can be appropriately selected in accordance with the object. Examples include phenyl, tolyl, xylyl, cuminyl, styryl, mesityl, cinnamyl, phenethyl, benzhydryl, and the like. These may be substituted by substituents.

The groups formed by four or fewer aromatic rings being bonded together are not particularly limited, and can be appropriately selected in accordance with the object. Examples include naphthyl, anthryl, phenanthryl, indenyl, azulenyl, benzanthracenyl, and the like. These may be substituted by substituents.

The groups having five or fewer condensed aromatic rings and whose total number of carbon, oxygen, nitrogen, and sulfur atoms is 30 or less are not particularly limited, and can be appropriately selected in accordance with the object. Examples include pyrrolyl, furyl, thienyl, pyridyl, quinolyl, isoquinolyl, imidazole, pyridinyl, pyrrolopyridinyl, thiazoyl, pyrimidinyl, thiophenyl, indolyl, quinolinyl, pyrinyl, adenyl, and the like, and may be substituted by substituents.

The aryl groups in the above aryloxy group, arylamino group, and diarylamino group are the same as the aforementioned aryl groups.

Suitable examples of the arylamino group are those expressed by the following formula for example.

In the formula, $Ar^1$ represents an aryl group. Examples of the aryl group are the aforementioned aryl groups. $R^{19}$ represents a hydrogen atom, or a straight chain, branched or cyclic alkyl group having from 1 to 10 carbon atoms. Examples of such alkyl groups are those listed above.

Suitable examples of the diarylamino group are those expressed by the following formula for example.

In the formula, $Ar^1$ and $Ar^2$ may be the same or different, and each represents an aryl group. Suitable examples of the aryl group are the above-listed aryl groups.

The dinaphthopyrene compound can be suitably used in an organic EL element, and can be suitably used in an organic thin-film layer, particularly a light-emitting layer or the like, of the organic EL element.

It is preferable that at least one of $R^1$ through $R^{18}$ is selected from aryl groups, arylamino groups and diarylamino groups. In this case, the dinaphthopyrene compound has the advantages that it has high color purity of green light and excellent light-emitting efficiency, light-emitting luminance and the like, and it can suitably be used in an organic EL element.

When at least one of $R^1$ through $R^{18}$ is an aryl group, the dinaphthopyrene compound is an aryl dinaphthopyrene compound having excellent electron transportability, and can suitably be used in at least one of an electron transporting layer and a light-emitting layer in the organic EL element. When at least one of $R^1$ through $R^{18}$ in above structural formula is an arylamino group, the dinaphthopyrene compound is an arylamino dinaphthopyrene compound having excellent positive hole (carrier) transportability. Moreover, when at least one of $R^1$ through $R^{18}$ in above structural formula is a diarylamino group, the dinaphthopyrene compound is a diarylamino dinaphthopyrene compound having excellent positive hole (carrier) transportability. Each can be suitably used in at least one of a positive hole transporting layer and a light-emitting layer in the organic EL element.

When, in structural formula, $R^1$, $R^3$ through $R^{16}$ and $R^{18}$ are hydrogen atoms and $R^2$ and $R^{17}$ are selected from phenyl groups, phenylamino groups, and diphenylamino groups (i.e., in the case of "structure 1"), the compound is stable. Therefore, the dinaphthopyrene compound can be suitably used in the organic EL element. $R^2$ and $R^{17}$ being the same is preferable from the standpoint that the effects are marked.

Similarly to above, in structural formula, a case in which $R^1$ through $R^2$ and $R^4$ through $R^{15}$ and $R^{17}$ through $R^{18}$ are hydrogen atoms and $R^3$ and $R^{16}$ are selected from phenyl groups, phenylamino groups, and diphenylamino groups (i.e., the case of "structure 2"), a case in which $R^1$ through $R^3$, $R^5$ through $R^{14}$, and $R^{16}$ through $R^{18}$ are hydrogen atoms and $R^4$ and $R^{15}$ are selected from phenyl groups, phenylamino groups, and diphenylamino groups (i.e., the case of "structure 3"), a case in which $R^1$ through $R^4$, $R^6$ through $R^{13}$, and $R^{15}$ through $R^{18}$ are hydrogen atoms and $R^5$ and $R^{14}$ are selected from phenyl groups, phenylamino groups, and diphenylamino groups (i.e., the case of "structure 4"), and the like are also preferable.

In structural formula, if the types and the numbers of the substituents are the same, the difference in the absorption peak wavelengths due to differences in the positions of the substituents is generally small. For example, when the absorption peak positions are estimated by molecular orbital computation using a molecular orbital computation program (WinMOPAC V3.0) manufactured by Fujitsu Ltd., in the case of a diphenylnaphthopyrene compound in which two substituents are phenyl groups in structures 1 through 4, the absorption peak wavelength of the diphenylnaphthopyrene compound of the structure 1 is 430 nm, the absorption peak wavelength of the diphenylnaphthopyrene compound of the structure 2 is 425 nm, the absorption peak wavelength of the diphenylnaphthopyrene compound of the structure 3 is 420 nm, and the absorption peak wavelength of the diphenylnaphthopyrene compound of the structure 4 is 413 nm.

The dinaphthopyrene compound of the present invention can suitably be used in various fields, and is particularly suitably used in the organic EL element and the organic EL display of the present invention which will be described hereinafter.

<Organic EL Element>

The organic EL element of the present invention comprises an organic thin-film layer including a light-emitting layer in between a positive electrode and a negative electrode, wherein the organic thin-film layer contains a dinaphthopyrene compound comprising a structure expressed below.

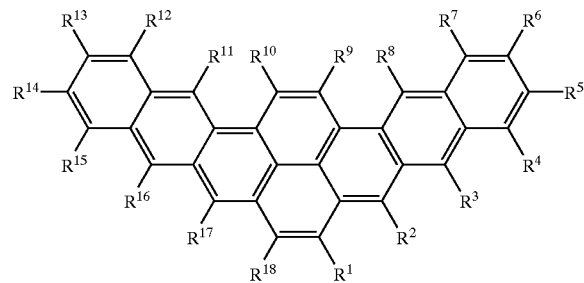

where $R^1$ through $R^{18}$ may be the same or may be different to each other, and represent hydrogen atoms or substituents. Examples of the substituents are those listed above.

The dinaphthopyrene compound is contained in the organic thin-film layer, is preferably contained in at least one of the electron transporting layer, the positive hole transporting layer, and the light-emitting layer in the organic thin-film layer, is more preferably contained in the light-emitting layer, and is particularly preferably contained in the electron transporting layer or in the light-emitting layer and the electron transporting layer, or in the positive hole transporting layer or in the light-emitting layer and the positive hole transporting layer.

When the dinaphthopyrene compound is contained in the light-emitting layer and the electron transporting layer or in the light-emitting layer and the positive hole transporting layer, the light-emitting layer and the electron transporting layer, or the light-emitting layer and the positive hole transporting layer, may be separate layers, or may be provided as a single layer which is a light-emitting and electron transporting layer, or which is a light-emitting and positive hole transporting layer.

As the dinaphthopyrene compound which is contained the light-emitting layer, it is preferable that at least one of $R^1$ through $R^{18}$ is selected from aryl groups, arylamino groups and diarylamino groups. It is more preferable that $R^1$, $R^3$ through $R^{16}$ and $R^{18}$ are hydrogen atoms and $R^2$ and $R^{17}$ are selected from phenyl groups, phenylamino groups and diphenylamino groups. It is particularly preferable that $R^2$ and $R^{17}$ are the same.

In these cases, in the above-described preferable cases, the organic EL element is advantageous with regard to the point that it has high color purity of green light and excellent light-emitting efficiency, light-emitting luminance and the like. In the above-described more preferable cases and particularly preferable cases, the dinaphthopyrene compound is stable, and therefore, the organic EL element is advantageous with respect to the fact that it has excellent durability.

As the arylamino group, those expressed by the above formula are preferable. As the diarylamino group, those expressed by the above formula are preferable.

In the dinaphthopyrene compound contained in the electron transporting layer, or contained in the electron transporting layer and the light-emitting layer, it is preferable that at least one of $R^1$ through $R^{18}$ is an aryl group. It is more preferable that $R^1$, $R^3$ through $R^{16}$ and $R^{18}$ are hydrogen atoms and $R^2$ and $R^{17}$ are phenyl groups, phenylamino groups and diphenylamino groups. It is particularly preferable that $R^2$ and $R^{17}$ are the same.

In these cases, in the above-described preferable cases, the dinaphthopyrene compound is an aryl dinaphthopyrene compound having excellent electron transportability. The organic EL element is advantageous with respect to the point that it has high color purity of green light and excellent light-emitting efficiency, light-emitting luminance and the like. In the above-described more preferable cases and particularly preferable cases, the dinaphthopyrene compound is stable, and therefore, the organic EL element is advantageous with respect to the fact that it has excellent durability.

In the dinaphthopyrene compound contained in the positive hole transporting layer, or contained in the positive hole transporting layer and the light-emitting layer, it is preferable that at least one of $R^1$ through $R^{18}$ is an aryl group. It is more preferable that $R^1$, $R^3$ through $R^{16}$ and $R^{18}$ are hydrogen atoms and $R^2$ and $R^{17}$ are phenyl groups, phenylamino groups and diphenylamino groups. It is particularly preferable that $R^2$ and $R^{17}$ are the same.

In these cases, in the above-described preferable cases, the dinaphthopyrene compound is an arylamino dinaphthopyrene compound or a diarylamino dinaphthopyrene compound having excellent positive hole (carrier) transportability. The organic EL element is advantageous with respect to the point that it has high color purity of green light and excellent light-emitting efficiency, light-emitting luminance and the like. In the above-described more preferable cases and particularly preferable cases, the dinaphthopyrene compound is stable, and therefore, the organic EL element is advantageous with respect to the fact that it has excellent durability.

It is preferable that the light-emitting layer contain, in addition to the dinaphthopyrene compound, a host compound.

The host compound is preferably a compound whose light-emitting wavelength is in the vicinity of the light absorption wavelength of the dinaphthopyrene compound. Among these, because the light absorption wavelength of the dinaphthopyrene compound is 350 to 530 nm, compounds, whose light absorption wavelength is at the shorter wavelength side of the dinaphthopyrene compound and whose light-emitting wavelength is in a vicinity of the light absorption wavelength of the dinaphthopyrene compound, are preferable. Specifically, the 4,4'-bis(9-carbazolyl)-biphenyl (CBP) (main light-emitting wavelength=380 nm) expressed by the following structural formula, 4,4'-bis(2,2'-diphenylvinyl)-1,1'-biphenyl (DPVBi) (main light-emitting wavelength=470 nm) expressed by the following structural formula, p-sexiphenyl (main light-emitting wavelength=400 nm) expressed by the following structural formula, 1,3,6,8-tetraphenylpyrene (main light-emitting wavelength=440 nm) expressed by the following structural formula, N,N'-dinaphthyl-N,N'-diphenyl-[1,1'-biphenyl]-4,4'-diamine (NPD) (main light-emitting wavelength=430 nm) expressed by the following structural formula, aluminum quinoline complex (Alq) (main light-emitting wavelength=530 nm), 9,9'-bianthryl (main light-emitting wavelength=460 nm) expressed by the following structural formula, and the like are preferable. The 4,4'-bis(9-carbazolyl)-biphenyl (CBP) is particularly preferable.

4,4'-bis(9-carbazolyl)-biphenyl (CBP)

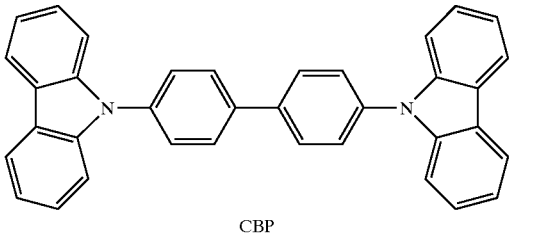

CBP

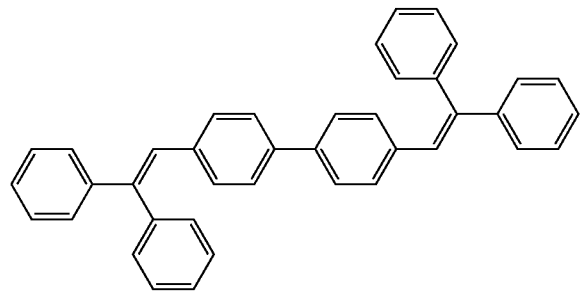

DPVBi

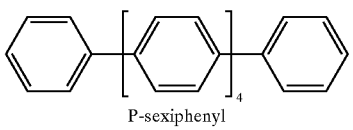

P-sexiphenyl

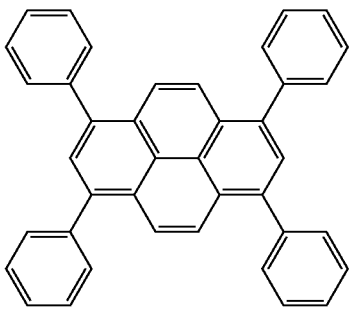

1,3,6,8-tetraphenylpyrene

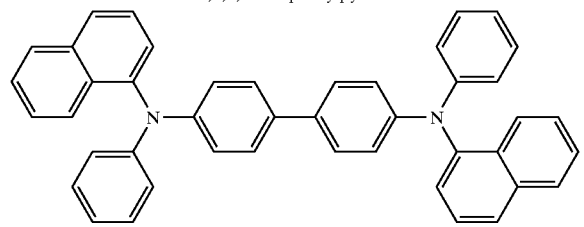

NPD

Aluminum quinoline complex (Alq)

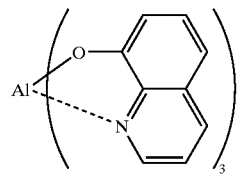

-continued

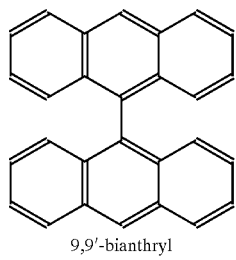
9,9'-bianthryl

The host compound, such as the 4,4'-bis(9-carbazolyl)-biphenyl (CBP) or the like, may have a substituent which is appropriately selected within a range in which the overlapping of the light-emitting wavelength of the host compound on the absorption wavelength of the dinaphthopyrene compound is not eliminated. For example, in the case of the 4,4'-bis(9-carbazolyl)-biphenyl (CBP), the methyl substituents, or the like can suitably be used.

When the light-emitting layer contains the host compound, a material having an excellent film forming ability can be selected as the host compound. Thus, there is the advantage that the light-emitting layer can have an excellent film forming ability regardless of the film forming ability of the dinaphthopyrene compound itself. Further, in the light-emitting layer, when the recombination site, at which the positive holes injected from the positive electrode and the electrons injected from the negative electrode recombine, is the host compound, first, the host compound is excited. Then, in cases in which the light-emitting wavelength of the host compound and the absorption wavelength of the guest compound (the dinaphthopyrene compound) overlap, the excitation energy effectively moves from the host compound to the guest compound (the dinaphthopyrene compound). The host compound returns to the ground state without emitting light, and only the guest compound (the dinaphthopyrene compound) which has moved to an excited state releases the excitation energy as green light. Thus, this is advantageous in that emission of green light of a high color purity is obtained, and the light-emitting efficiency, light-emitting luminance and the like are excellent. Generally when the light emitting molecules exist alone or in high density in the thin layer, generates an interaction between the light emitting molecules referred to as "concentration quenching" which is a light emission efficiency deterioration phenomenon caused by the molecules coming in closer contact with each other. However, in the aforementioned light-emitting layer, the dinaphthopyrene compound is dispersed at a relatively low concentration in the host compound, the aforementioned "concentration quenching" is effectively suppressed, and the light-emitting efficiency is excellent.

The light-emitting layer may contain n types of host compounds (wherein n represents an integer of 1 or more). In this case, given that the n types of host compounds are the first host compound, the second host compound, . . . , the (n−1)th host compound, and the nth host compound in order from the host compound with the shortest light-emitting wavelength, it is preferable that the light-emitting wavelength of the first host compound is in a vicinity of the light absorption wavelength of the second host compound, the light-emitting wavelength of the second host compound is in a vicinity of the light absorption wavelength of the third host compound, . . . , the light-emitting wavelength of the (n−1)th host compound is in a vicinity of the light absorption wavelength of the nth host compound, and the light-emitting wavelength of the nth host compound is in a vicinity of the light absorption wavelength of the dinaphthopyrene compound.

When the light-emitting layer contains n types of host compounds, materials having an excellent film forming ability can be selected as the first host compound through the nth host compound. Thus, there is the advantage that the light-emitting layer can have an excellent film forming ability regardless of the film forming ability of the dinaphthopyrene compound itself. Further, in the light-emitting layer, when the recombination site, at which the positive holes injected from the positive electrode and the electrons injected from the negative electrode recombine, is the kth host compound, first, the kth host compound is excited. Then, in a case in which the light-emitting wavelength of the kth host compound and the absorption wavelength of the (k+1)th host compound overlap, and the light-emitting wavelength of the (k+1)th host compound and the absorption wavelength of the (k+2)th host compound overlap, . . . , and the light-emitting wavelength of the nth host compound and the absorption wavelength of the guest compound (the dinaphthopyrene compound) overlap, the excitation energy effectively moves from the host compounds to the guest compound (the dinaphthopyrene compound). The host compounds return to the ground state without emitting light, and only the guest compound (the dinaphthopyrene compound) which has moved to an excited state releases the excitation energy as green light. Thus, this is advantageous in that emission of green light of a high color purity is obtained, and the light-emitting efficiency, light-emitting luminance and the like are excellent. Further, at the light-emitting layer, the dinaphthopyrene compound is dispersed at a relatively low concentration in the first host compound through the nth host compound, the aforementioned "concentration quenching" is effectively suppressed, and the light-emitting efficiency is excellent.

The amount of the host compound contained in the light-emitting layer is, with respect to 1 mol of the dinaphthopyrene compound, usually around 4 mol or more, and 10 mol or more is preferable, and 50 mol or more is more preferable.

When the amount of the host compound contained in the light-emitting layer is around 4 mol % or more, improvement in the light-emitting efficiency, light-emitting luminance, and the like of the dinaphthopyrene compound can be seen. In the preferable range, the improvement is sufficient, and in the aforementioned more preferable range, the improvement is marked.

When there are n types of host compounds, among the n types of host compounds and preferably among two types of host compounds, the contained amount in the light-emitting layer of the host compound which has a light-emitting wavelength in a vicinity of the absorption wavelength of the dinaphthopyrene compound is, with respect to 1 mol of the dinaphthopyrene compound, preferably about 0.5 mol or more, and more preferably 1 mol or more, and particularly preferably 3 mol or more.

When the contained amount of the host compound in the light-emitting layer is around 0.5 mol % or more, improvement in the light-emitting efficiency, light-emitting luminance, and the like of the dinaphthopyrene compound can be seen. In the preferable range, the improvement is sufficient, and in the aforementioned more preferable range, the improvement is marked.

The light-emitting layer in the organic EL element of the present invention can, at the time an electrical field is applied, inject positive holes from the positive electrode, a positive hole injecting layer, the positive hole transporting layer or the like, and can inject electrons from the negative electrode, an electron injecting layer, the electron transporting layer or the like, and provides a site for recombination of the positive holes and the electrons. It suffices for the light-emitting layer to have the function of making the dinaphthopyrene compound (light-emitting molecules), which exhibits emission of green light, emit light due to the recombination energy which is generated at the time of recombination. The light-emitting layer may, in addition to the dinaphthopyrene compound, contain another light-emitting material provided that the aforementioned emission of green light does not deteriorate.

Suitable examples of the other light-emitting material are materials which exhibit emission of green light. Examples include the quinacridone compound disclosed in JP-A No. 5-70773, the hydroxybenzoquinoline metal complexes disclosed in JP-A No. 6-322362, and the like.

The other light-emitting material may be contained in the same layer as the dinaphthopyrene compound, or may be contained in a different layer. In the latter case, the light-emitting layer has a multilayer structure.

The light-emitting layer can be formed in accordance with known methods. For example, the light-emitting layer can be suitably formed by a vapor deposition method, a wet-type film forming method, an MBE (molecular beam epitaxy) method, a cluster ion beam method, a molecule accumulating method, an LB method, a printing method, a transfer method, or the like.

Among these, a vapor deposition method is preferable from the standpoints that no organic solvents are used and the problem of waste liquid processing does not arise, and that the vapor deposition method is inexpensive and easy, and efficient manufacturing can be carried out. However, in a case in which the organic thin-film layer is designed to be a single layer structure, for example, in a case in which the organic thin-film layer is formed as a positive hole transporting and light-emitting and electron transporting layer, a wet-type film forming method is preferable.

The vapor deposition method is not particularly limited, and can be appropriately selected from known vapor deposition methods in accordance with the object. Examples include a vacuum vapor deposition method, a low resistance heating vapor deposition method, a chemical vapor deposition method, a physical vapor deposition method, and the like. Examples of the chemical vapor deposition method are a plasma CVD method, a laser CVD method, a heat CVD method, a gas source CVD method, and the like. Formation of the light-emitting layer by a vapor deposition method can suitably be carried out by, for example, vacuum vapor deposition of the dinaphthopyrene compound, and in a case in which the light-emitting layer contains a host compound in addition to the dinaphthopyrene compound, by simultaneously depositing the dinaphthopyrene compound and the host compound by vacuum vapor deposition.

The wet-type film forming method is not particularly limited, and can be appropriately selected from known wet-type film forming methods in accordance with the object. Examples include an ink jet method, a spin coating method, a kneader coating method, a bar coating method, a blade coating method, a casting method, a dipping method, a curtain coating method, and the like.

In the case of the wet-type film forming method, a solution in which the material of the light-emitting layer is dissolved or dispersed together with a resin component can be used (can be applied or the like). Examples of the resin component include polyvinyl carbazole, polycarbonate, polyvinyl chloride, polystyrene, polymethyl methacrylate, polyester, polysulfone, polyphenylene oxide, polybutadiene, hydrocarbon resin, ketone resin, phenoxy resin, polyamide, ethyl cellulose, vinyl acetate, ABS resin, polyurethane, melamine resin, unsaturated polyester resin, alkyd resin, epoxy resin, silicone resin, and the like.

Formation of the light-emitting layer by a wet-type film forming method may suitably be carried out, for example, by using (applying and drying) a solution (coating liquid) in which the dinaphthopyrene compound and the resin material (which is used as needed) are dissolved in a solvent, or, in a case in which the light-emitting layer contains a host compound in addition to the dinaphthopyrene compound, by using (applying and drying) a solution (coating liquid) in which the dinaphthopyrene compound, the host compound and the resin material (which is used as needed) are dissolved in a solvent.

The thickness of the light-emitting layer is preferably 1 to 50 nm, and more preferably 3 to 20 nm.

When the thickness of the light-emitting layer falls within the above preferable numerical range, the purity of the green light emitted by the organic EL element is high, and the light-emitting efficiency and light-emitting luminance are sufficient. When the thickness of the light-emitting layer falls within the above more preferable numerical range, these features are marked.

The organic EL element of the present invention has, between the positive electrode and the negative electrode, an organic thin-film layer which contains the light-emitting layer. The organic EL element may include other layers, such as a protective layer or the like, in accordance with the object.

The organic thin-film layer has at least the light-emitting layer, and if needed, may also include a positive hole injecting layer, a positive hole transporting layer, an electron transporting layer, or the like.

—Positive Electrode—

The positive electrode is not particularly limited, and can be appropriately selected in accordance with the object. The positive electrode preferably can supply positive holes (carrier) to the organic thin-film layer. Specifically, when the organic thin-film layer has only the light-emitting layer, it is preferable that the positive electrode can supply positive holes to the light-emitting layer. When the organic thin-film layer also has a positive hole transporting layer, it is preferable that the positive electrode can supply positive holes to the positive hole transporting layer. When the organic thin-film layer also has a positive hole injecting layer, it is preferable that the positive electrode can supply positive holes (or carrier) to the positive hole injecting layer.

The material of the positive electrode is not particularly limited, and may be selected appropriately in accordance with the object. Examples include metals, alloys, metal oxides, electrically conductive compounds, mixtures thereof, and the like. Among these, materials with a work function of 4 eV or more are preferable.

Concrete examples of the material of the positive electrode are electrically conductive metal oxides such as tin oxide, zinc oxide, indium oxide, indium tin oxide (ITO), and the like; metals such as gold, silver, chromium, nickel, or the like; mixtures or layered structures of these metals and electrically conductive metal oxides; inorganic electrically conductive substances such as copper iodide, copper sulfide, and the like; organic electrically conductive materials such as polyaniline, polythiophene, polypyrrole, and the like; layered structures of these materials and ITO; and the like. A single one of these materials may be used, or two or more materials may be used in combination. Among these, electrically conductive metal oxides are preferable, and ITO is particularly preferable from the standpoints of produceability, high conductivity, transparency, and the like.

The thickness of the positive electrode is not particularly limited, and can be appropriately selected in accordance with the material and the like. However, a thickness of 1 to 5000 nm is preferable, and a thickness of 20 to 200 nm is more preferable.

The positive electrode is usually formed on a substrate formed of a glass such as soda lime glass, non-alkali glass or the like; a transparent resin; or the like.

When a glass is used as the substrate, a non-alkali glass, or a soda lime glass which has been subjected to barrier coating treatment with silica or the like, is preferable from the standpoint of few eluted ions from the glass.

The thickness of the substrate is not particularly limited provided that it is thickness sufficient to maintain the mechanical strength. When a glass is used as the substrate, the thickness is usually 0.2 mm or more, and 0.7 mm or more is preferable.

The positive electrode can be suitably formed by the above-described methods such as, for example, a vapor deposition method, a wet-type film forming method, an electron beam method, a sputtering method, a reactive sputtering method, an MBE (molecular beam epitaxy) method, a cluster ion beam method, an ion plating method, a plasma polymerization method (high-frequency excited ion plating method), a molecule accumulating method, an LB method, a printing method, a transfer method, a method of coating a dispersion of ITO by a chemical reaction method (a sol-gel method or the like), or the like.

By carrying out washing or other processings on the positive electrode, the driving voltage of the organic EL element can be lowered, and the light-emitting efficiency can be increased. Suitable examples of the other processings include, in the case in which the material of the positive electrode is ITO for example, UV-ozone processing, plasma processing, or the like.

—Negative Electrode—

The negative electrode is not particularly limited, and can be appropriately selected in accordance with the object. The negative electrode preferably can supply electrons to the organic thin-film layer. Specifically, when the organic thin-film layer has only the light-emitting layer, it is preferable that the negative electrode can supply electrons to the light-emitting layer. When the organic thin-film layer also has an electron transporting layer, it is preferable that the negative electrode can supply electrons to the electron transporting layer. When there is an electron injecting layer between the organic thin-film layer and the negative electrode, it is preferable that the negative electrode can supply electrons to the electron injecting layer.

The material of the negative electrode is not particularly limited, and can be appropriately selected in accordance with the adhesion between the negative electrode and the layers or molecules adjacent thereto such as the electron transporting layer, the light-emitting layer, and the like, the ionization potential, the stability, and the like. Examples are metals, alloys, metal oxides, electrically conductive compounds, mixtures thereof, and the like.

Specific examples of the material of the negative electrode are alkali metals (e.g., Li, Na, K, Cs, and the like), alkaline earth metals (e.g., Mg, Ca, and the like), gold, silver, lead, aluminum, sodium-potassium alloys or mixed metals thereof, lithium-aluminum alloys or mixed metals thereof, magnesium-silver alloys or mixed metals thereof, rare earth metals such as indium, ytterbium, or the like, alloys thereof, and the like.

A single type of these materials may be used, or a combination of two or more types may be used. Among these, materials having a work function of 4 eV or less are preferable. Aluminum, lithium-aluminum alloys or mixed metals thereof, magnesium-silver alloys or mixed metals thereof, and the like are more preferable.

The thickness of the negative electrode is not particularly limited, and may be appropriately selected in accordance with the material of the negative electrode or the like. The thickness is preferably 1 to 10,000 nm, and 20 to 200 nm is more preferable.

The negative electrode can suitably be formed by the above-described methods such as, for example, a vapor deposition method, a wet-type film forming method, an electron beam method, a sputtering method, a reactive sputtering method, an MBE (molecular beam epitaxy) method, a cluster ion beam method, an ion plating method, a plasma polymerization method (high-frequency excited ion plating method), a molecule accumulating method, an LB method, a printing method, a transfer method, or the like.

When two or more types of materials are used in combination as the material of the negative electrode, the two or more types of materials may be vapor deposited simultaneously such that an alloy electrode or the like is formed, or an alloy which is prepared in advance may be vapor deposited such that an alloy electrode or the like is formed.

For the values of resistance of the positive electrode and the negative electrode, lower values are preferable. It is preferable that the values of resistance are several hundred Ω/□ or less.

—Positive Hole Injecting Layer—

The positive hole injecting layer is not particularly limited, and may be appropriately selected in accordance with the object. For example, it is preferable that the positive hole injecting layer has the function of injecting positive holes from the positive electrode at the time when an electrical field is applied.

The material of the positive hole injecting layer is not particularly limited, and may be appropriately selected in accordance with the object. Suitable examples include copper phthalocyanine, polyaniline, starburst amine expressed by the following formula, and the like.

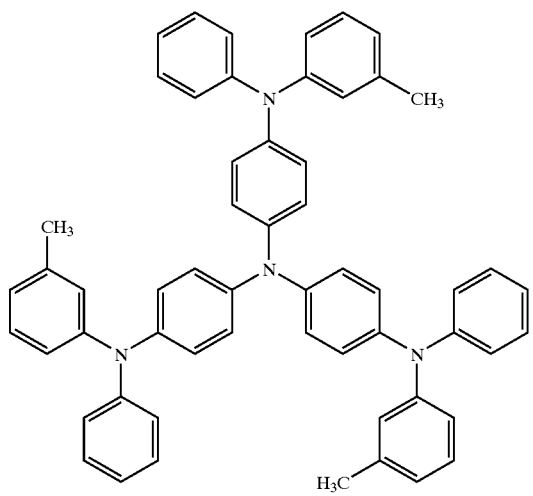

The thickness of the positive hole injecting layer is not particularly limited, and may be appropriately selected in accordance with the object. For example, a thickness of about 1 to 100 nm is preferable, and 5 to 50 nm is more preferable.

The positive hole injecting layer can suitably be formed by the above-described methods such as, for example, a vapor deposition method, a wet-type film forming method, an electron beam method, a sputtering method, a reactive sputtering method, an MBE (molecular beam epitaxy) method, a cluster ion beam method, an ion plating method, a plasma polymerization method (high-frequency excited ion plating method), a molecule accumulating method, an LB method, a printing method, a transfer method, or the like.

—Positive Hole Transporting Layer—

The positive hole transporting layer is not particularly limited, and may be appropriately selected in accordance with the object. For example, a layer which has either a function of transporting positive holes from the positive electrode at the time when an electrical field is applied, or a function of blocking electrons which are injected from the negative electrode, is preferable.

As described above, the dinaphthopyrene compound may be used as the material of the positive hole transporting layer. Materials other than the dinaphthopyrene compound are not particularly limited and may be appropriately selected in accordance with the object. Examples include aromatic amine compounds, carbazole, imidazole, triazole, oxazole, oxadiazole, polyaryl alkane, pyrazoline, pyrazolone, phenylene diamine, aryl amine, amine-substituted chalcone, styryl anthracene, fluorenon, hydrazone, stilbene, silazane, styryl amine, aromatic dimethylidine compound, porphyrin compounds, polysilane compounds, poly(N-vinylcarbazole), aniline copolymers, thiophene oligomers and polymers, electrically conductive macromolecular oligomers and polymers such as polythiophene and the like, carbon film, and the like.

A single one of these substances can be used, or two or more types may be used in combination. Among these, aromatic amine compounds are preferable, and specifically TPD (N,N'-diphenyl-N,N'-bis(3-methylphenyl)-[1,1'-biphenyl]-4,4'-diamine) expressed by the following formula, and NPD (N,N'-dinaphthyl-N,N'-diphenyl-[1,1'-biphenyl]-4,4'-diamine) expressed by the following formula, and the like are more preferable.

TPD

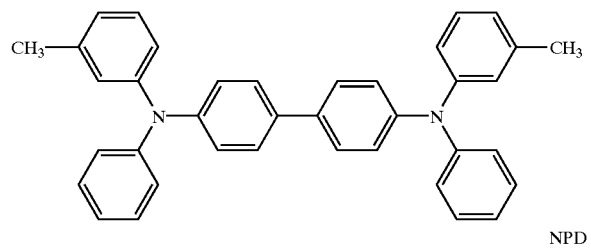

NPD

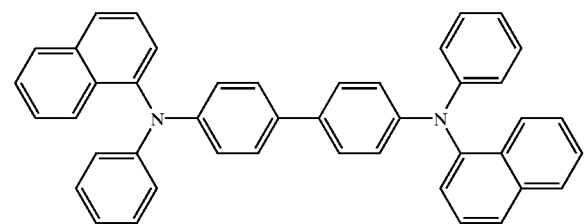

The thickness of the positive hole transporting layer is not particularly limited, and may be appropriately selected in accordance with the object. The thickness is usually 1 to 500 nm, and a thickness of 10 to 100 nm is preferable.

The positive hole transporting layer can suitably be formed by the above-described methods such as, for example, a vapor deposition method, a wet-type film forming method, an electron beam method, a sputtering method, a reactive sputtering method, an MBE (molecular beam epitaxy) method, a cluster ion beam method, an ion plating method, a plasma polymerization method (high-frequency excited ion plating method), a molecule accumulating method, an LB method, a printing method, a transfer method, or the like.

—Electron Transporting Layer—

The electron transporting layer is not particularly limited, and may be appropriately selected in accordance with the object. For example, a layer which has either a function of transporting electrons from the negative electrode, or a function of blocking positive holes which are injected from the positive electrode, is preferable.

As described above, the dinaphthopyrene compound may be used as the material of the electron transporting layer. Materials other than the dinaphthopyrene compound are not particularly limited and may be appropriately selected in accordance with the object. Examples include quinoline derivatives of organic metal complexes or the like whose ligands are 8-quinolinols such as tris(8-quinolinolato) aluminum (Alq) or derivatives thereof, oxadiazole derivatives, triazole derivatives, phenanthroline derivatives, perylene derivatives, pyridine derivatives, pyrimidine derivatives, quinoxaline derivatives, diphenylquinone derivatives, nitro-substituted fluorene derivatives, and the like.

The thickness of the electron transporting layer is not particularly limited, and may be appropriately selected in accordance with the object. The thickness is usually around 1 to 500 nm, and 10 to 50 nm is preferable.

The electron transporting layer may be a single-layer structure, or may be a laminated layer structure.

The electron transporting layer can suitably be formed by the above-described methods such as, for example, a vapor deposition method, a wet-type film forming method, an electron beam method, a sputtering method, a reactive sputtering method, an MBE (molecular beam epitaxy) method, a cluster ion beam method, an ion plating method, a plasma polymerization method (high-frequency excited ion plating method), a molecule accumulating method, an LB method, a printing method, a transfer method, or the like.

—Other Layers—

The organic EL element of the present invention may have other layers which are appropriately selected in accordance with the object. Suitable examples of other layers are a protective layer and the like.

The protective layer is not particularly limited, and may be appropriately selected in accordance with the object. For example, a layer which can suppress the penetration, into the organic EL element, of molecules and substances which promote deterioration of the organic EL element, such as moisture, oxygen, and the like, is preferable.

Examples of the material of the protective layer are metals such as In, Sn, Pb, Au, Cu, Ag, Al, Ti, Ni, and the like, metal oxides such as MgO, SiO, $SiO_2$, $Al_2O_3$, GeO, NiO, CaO, BaO, $Fe_2O_3$, $Y_2O_3$, $TiO_2$, and the like, nitrides such as SiN, $SiN_xO_y$, and the like, metal fluorides such as $MgF_2$, LiF, $AlF_3$, $CaF_2$, and the like, polyethylene, polypropylene, polymethylmethacrylate, polyimide, polyurea, polytetrafluoroethylene, polychlorotrifluoroethylene, polydichlorodifluoroethylene, copolymers of chlorotrifluoroethylene and dichlorodifluoroethylene, copolymers obtained by copolymerizing a monomer mixture containing tetrafluoroethylene and at least one type of co-monomer, fluorine-containing copolymers having a cyclic structure in the copolymerized main chain, water-absorbent substances whose coefficient of water absorption is 1% or more, moisture-proof substances whose coefficient of water absorption is 0.1% or less, and the like.

The protective layer can suitably be formed by the above-described methods such as, for example, a vapor deposition method, a wet-type film forming method, a sputtering method, a reactive sputtering method, an MBE (molecular beam epitaxy) method, a cluster ion beam method, an ion plating method, a plasma polymerization method (high-frequency excited ion plating method), a printing method, a transfer method, or the like.

The structure of the organic EL element of the present invention is not particularly limited, and may be appropriately selected in accordance with the object. Suitable examples of the layer structure are the following layer structures (1) through (13): (1) positive electrode/positive hole injecting layer/positive hole transporting layer/light-emitting layer/electron transporting layer/electron injecting layer/negative electrode, (2) positive electrode/positive hole injecting layer/positive hole transporting layer/light-emitting layer/electron transporting layer/negative electrode, (3) positive electrode/positive hole transporting layer/light-emitting layer/electron transporting layer/ electron injecting layer/negative electrode, (4) positive electrode/positive hole transporting layer/light-emitting layer/electron transporting layer/negative electrode, (5) positive electrode/positive hole injecting layer/positive hole transporting layer/light-emitting and electron transporting layer/electron injecting layer/negative electrode, (6) positive electrode/positive hole injecting layer/positive hole transporting layer/light-emitting and electrode transporting layer/ negative electrode, (7) positive electrode/positive hole transporting layer/light-emitting and electron transporting layer/ electron injecting layer/negative electrode, (8) positive electrode/positive hole transporting layer/light-emitting and electron transporting layer/negative electrode, (9) positive electrode/positive hole injecting layer/positive hole transporting and light-emitting layer/electron transporting layer/ electron injecting layer/negative electrode, (10) positive electrode/positive hole injecting layer/positive hole transporting and light-emitting layer/electron transporting layer/ negative electrode, (11) positive electrode/positive hole transporting and light-emitting layer/electron transporting layer electron injecting layer/negative electrode, (12) positive electrode/positive hole transporting and light-emitting layer/electron transporting layer/negative electrode, (13) positive electrode/positive hole transporting and light-emitting and electron transporting layer/negative electrode, and the like.

Among these layer structures, when (4) positive electrode/positive hole transporting layer/light-emitting layer/electron transporting layer/negative electrode is illustrated, it is as in FIG. 1. An organic EL element 10 has a layer structure in which a positive electrode 14 (e.g., an ITO electrode) formed on a glass substrate 12, a positive hole transporting layer 16, a light-emitting layer 18, an electron transporting layer 20, and a negative electrode 22 (e.g., an Al—Li electrode) are layered in that order. The positive electrode 14 (e.g., an ITO electrode) and the negative electrode 22 (e.g., an Al—Li electrode) are connected to each other via a power source. An organic thin-film layer 26 for emitting green light is formed by the positive hole transporting layer 16, the light-emitting layer 18, and the electron transporting layer 20.

As the emission wavelength of the organic EL element of the present invention, 490 to 560 nm is preferable, and 510 to 540 nm is more preferable.

With regard to the light-emitting efficiency of the organic EL element of the present invention, the organic EL element desirably emits green light at a voltage of 10V or less, and preferably emits green light at 7V or less, and more preferably emits green light at 5V or less.

At an applied voltage of 10V, the light-emitting luminance of the organic EL element of the present invention is preferably 100 $cd/m^2$ or more, and is more preferably 500 $cd/m^2$ or more, and is particularly preferably 1000 $cd/m^2$ or more.

The organic EL element of the present invention can be suitably used in various types of fields such as, for example, computers, vehicle-mounted display devices, outdoor display devices, machines for household use, machines for industrial use, machines for home electronics, traffic-related display devices, clock display devices, calendar display devices, luminescent screens, sound machines, and the like. The organic EL element of the present invention can particularly preferably be used in the organic EL display of the present invention which will be described hereinafter.

<Organic EL Display>

The organic EL display of the present invention is not particularly limited, other than that it utilizes the organic EL element of the present invention, and can appropriately utilize known structures.

The organic EL display of the present invention may emit only light of the single color of green, or may be a full-color type display which emits lights of multiple colors.

As methods for making the organic EL display a full-color type display, for example, as disclosed in "Gekkan Display", September 2000, pp. 33–37, there are a three-color light-emitting method in which organic EL elements, which emit lights corresponding to the three primary colors (blue (B), green (G), red (R)), respectively, are disposed on a substrate; a white color method in which white light emitted by an organic EL element for emitting white light is passed through a color filter so as to be divided into the three primary colors; a color conversion method in which blue light emitted by an organic EL element for emitting blue light is passed through a fluorescent dye layer and converted into red (R) and green (G); and the like. However, because the organic EL element of the present invention which is used is for emitting green light, the present invention can particularly suitably utilize the three-color light-emitting method.

When manufacturing a full-color type organic EL display by the three-color light-emitting method, in addition to the organic EL element of the present invention which is for emitting green light, an organic EL element for emitting red light and an organic EL element for emitting blue light are needed.

The organic EL element for emitting red light is not particularly limited, and can be appropriately selected from among known elements. For example, an element whose layer structure is ITO (positive electrode)/NPD/DCJTB expressed by the following structural formula 1% aluminum quinoline complex (Alq)/the Alq/Al—Li (negative electrode), or the like is suitable. The DCJTB is 4-dicyanomethylene-6-cp-julolidinostyryl-2-tert-butyl-4H-pyran.

DCJTB

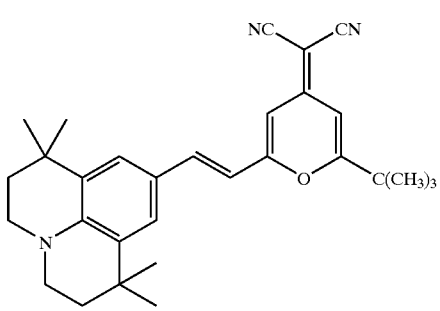

The organic EL element for emitting blue light is not particularly limited, and can be appropriately selected from among known elements. For example, an element whose layer structure is ITO (positive electrode)/NPD/DPVBi expressed by the following formula/Alq/Al—Li (negative electrode), or the like is suitable. DPVBi is 4,4'-bis(2,2'-diphenyl-ethane-1-yl)-biphenyl.

DPVBi

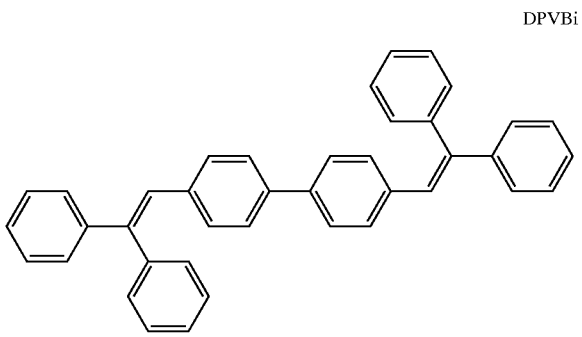

The mode of the organic EL display is not particularly limited, and can be appropriately selected in accordance with the object. Suitable examples include a passive matrix panel, an active matrix panel, and the like, such as those disclosed in "Nikkei Electronics", No. 765, Mar. 13, 2000, pp. 55–62.

Figure 2:
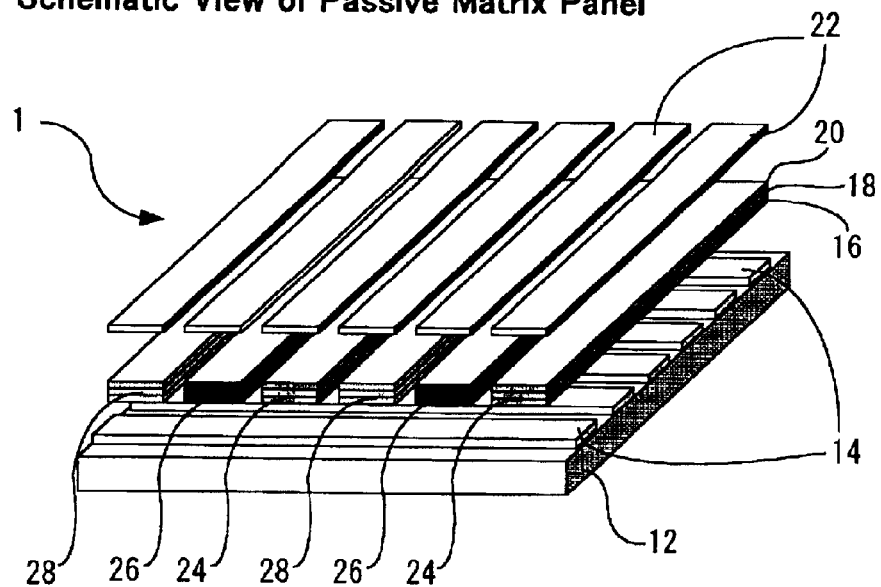
FIG. 2 is a schematic explanatory view for explaining a structural example of a passive matrix type organic EL display (passive matrix panel).

The passive matrix panel has, as shown in FIG. 2 for example, the strip-shaped positive electrodes 14 (e.g., ITO electrodes), which are disposed in parallel, on the glass substrate 12. The passive matrix panel has, on the positive electrodes 14, the strip-shaped organic thin-film layers 24 for emitting red light, strip-shaped organic thin-film layers 26 for emitting green light, and strip-shaped organic thin-film layers 28 for emitting blue light, which are disposed in order and parallel to each other and in a direction substantially orthogonal to the positive electrodes 14. The passive matrix panel has, on the organic thin-film layers 24 for emitting red light, the organic thin-film layers 26 for emitting green light, and the organic thin-film layers 28 for emitting blue light, the negative electrodes 22 having the same configurations as the organic thin-film layers 24, 26, 28.

Figure 3:
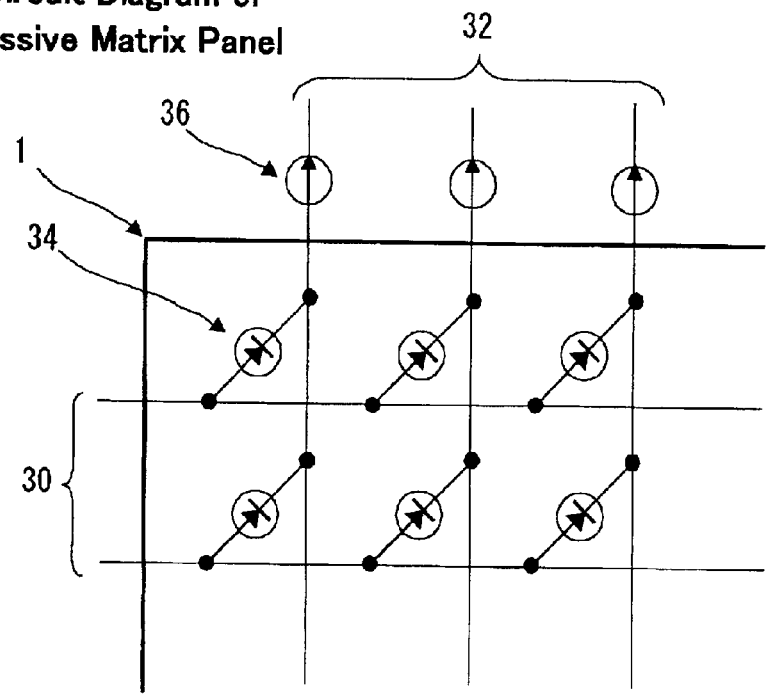
FIG. 3 is a schematic explanatory view for explaining circuits in the passive matrix type organic EL display (passive matrix panel) shown in FIG. 2.

At the passive matrix panel, as shown in FIG. 3 for example, a positive electrode line 30 formed from a plurality of the positive electrodes 14, and a negative electrode line 32 formed from a plurality of the negative electrodes 22, intersect one another in substantially orthogonal directions so as to form a circuit. The respective organic thin-film layers 24, 26, 28 for emitting red light, green light, and blue light, which are positioned at the respective points of intersection, function as pixels. A plurality of organic EL elements 34 exist in correspondence with the respective pixels. At the passive matrix panel, when current is applied by a constant current source 36 to one of the positive electrodes 14 in the positive electrode line 30 and one of the negative electrodes 22 in the negative electrode line 32, at that time, current is applied to the organic EL thin-film layer which is positioned at that point of intersection, and the organic EL thin-film layer at that position emits light. By controlling the emission of light of the pixel units, a full-color image can easily be formed.

Figure 4:
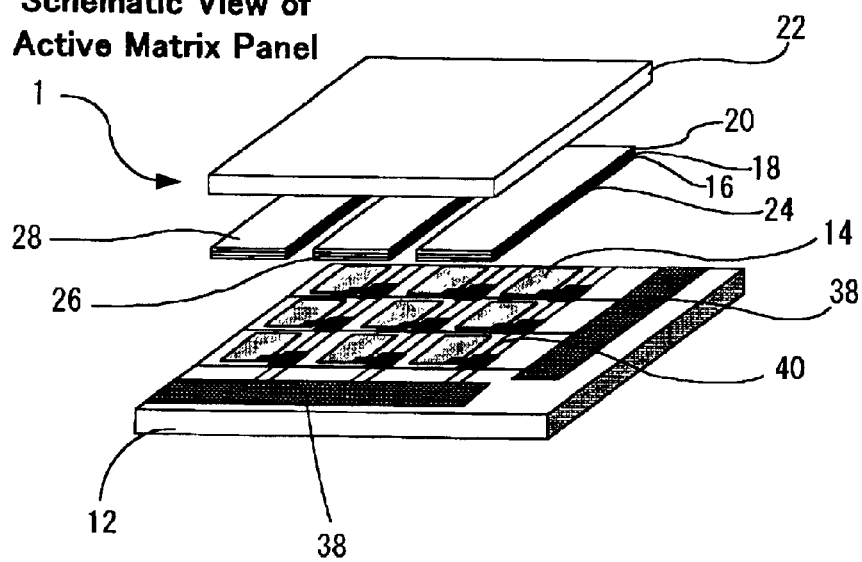
FIG. 4 is a schematic explanatory view for explaining a structural example of an active matrix type organic EL display (active matrix panel).

As shown in FIG. 4 for example, in the active matrix panel, scan lines, data lines, and current supplying lines are formed in a gridiron layout on the glass substrate 12. The active matrix panel has TFT circuits 40, which are connected to the scan lines and the like forming the gridiron layout and which are disposed in the respective squares of the grid, and the positive electrodes 14 (e.g., ITO electrodes) which can be driven by the TFT circuits 40 and which are disposed within the respective grids. The active matrix panel has, on the positive electrodes 14, the strip-shaped organic thin-film layers 24 for emitting red light, the strip-shaped organic thin-film layers 26 for emitting green light, and the strip-shaped organic thin-film layers 28 for emitting blue light, which are disposed in order and parallel to each other. The active matrix panel has, on the organic thin-film layers 24 for emitting red light, the organic thin-film layers 26 for emitting green light, and the organic thin-film layers 28 for emitting blue light, the negative electrode 22 which is disposed so as to cover all of the organic thin-film layers 24, 26, 28. The organic thin-film layers 24 for emitting red light, the organic thin-film layers 26 for emitting green light, and the organic thin-film layers 28 for emitting blue light each have the positive hole transporting layer 16, the light-emitting layer 18, and the electron transporting layer 20.

Figure 5:
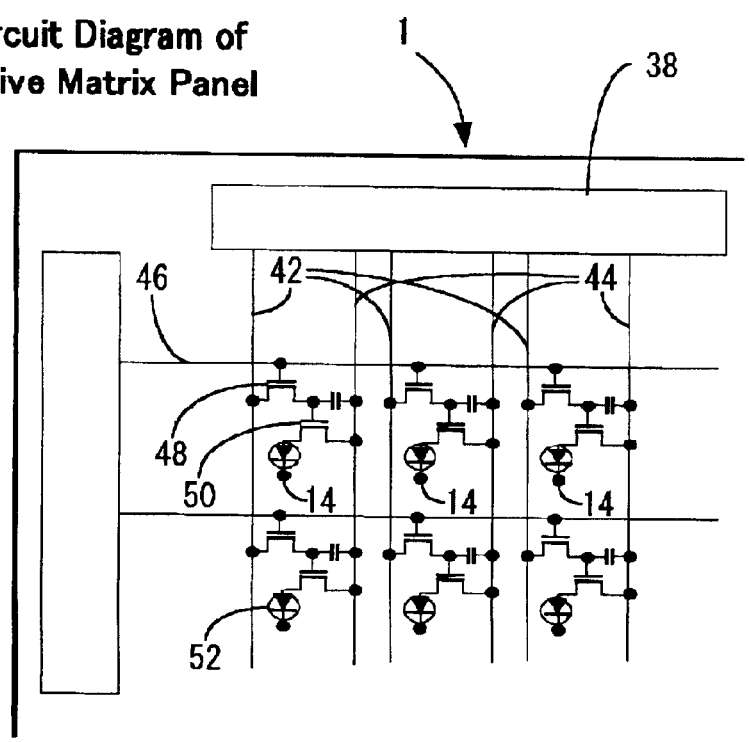
FIG. 5 is a schematic explanatory view for explaining circuits in the active matrix type organic EL display (active matrix panel) shown in FIG. 4.

In the active matrix panel, as shown in FIG. 5 for example, a plurality of scan lines 46 which are provided parallel, and a plurality of data lines 42 and current supplying lines which are provided parallel, are orthogonal to one another so as to form a gridiron layout. A TFT 48 for switching and a TFT 50 for driving are connected to form a circuit in each square of the gridiron. When current is applied from a driving circuit 38, the TFT 48 for switching and the TFT 50 for driving can be driven per square of the gridiron. In each square of the gridiron, the organic thin-film layers 24, 26, 28 for emitting red light, green light and blue light function as pixels. At the active matrix panel, when voltage is applied from the driving circuit 38 to one of the scan lines 46 disposed in the lateral direction and the current supplying line 44 disposed in the lengthwise direction, at that time, the TFT 48 for switching which is positioned at that point of intersection is driven, and accompanying this driving, the TFT 50 for driving is driven, and an organic EL element 52 at that position emits light. By controlling the emission of light of the pixel units, a full-color image can easily be formed.

The organic EL display of the present invention can be suitably used in various types of fields such as, for example, computers, vehicle-mounted display devices, outdoor display devices, machines for household use, machines for industrial use, machines for home electronics, traffic-related display devices, clock display devices, calendar display devices, luminescent screens, sound machines, and the like.

EXAMPLES

Hereinafter, Examples of the present invention will be concretely described. However, the present invention is not to be limited in any way to these Examples.

Synthesis Example 1
Synthesis of dinaphtho(2':3'-3:4)(2":3"-9:10)pyrene

Dinaphtho(2':3'-3:4)(2":3"-9:10)pyrene expressed by the following formula is synthesized in accordance with a publication ("Journal of the Chemical Society", 1949, p. 2013).

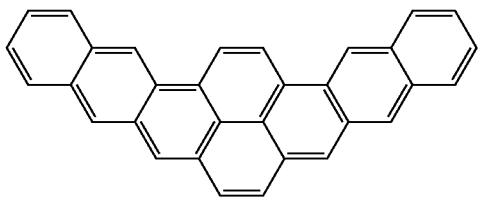

Synthesis Example 2
Synthesis of 5,8-diphenyl-dinaphtho(2':3'-3:4)(2":3"-9:10)pyrene Dinaphtho(2':3'-3:4)(2":3"-9:10)pyrene is dissolved in carbon tetrachloride. While the resultant mixture is being cooled, 1 mol equivalent of bromine is added thereto. The mixture is reacted for 4 hours and brominated. Thereafter, the mixture is purified in accordance with a usual method, and 5,8-dibromodinaphtho(2':3'-3:4)(2":3"-9:10)pyrene is obtained. 2 mol equivalent of phenylboronic acid [Ph-B(OH)$_2$] (where "Ph" represents a phenyl group) is refluxed and reacted for twelve hours with the 5,8-dibromodinaphtho(2':3'-3:4)(2":3"-9:10)pyrene obtained in this way, in a xylene/2M sodium carbonate aqueous solution, by using 0.01 mol equivalent of tetrakis(triphenylphosphine) palladium (0) [Pd(PPh$_3$)$_4$] (where "Ph" represents a phenyl group) as a catalyst. Thereafter, the resultant mixture is purified in accordance with a usual method, and the 5,8-diphenyl-dinaphtho(2':3'-3:4)(2":3"-9:10)pyrene expressed by the following formula is synthesized. (Note that, in the formula, "Ph" represents a phenyl group.)

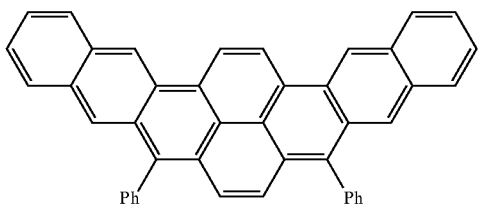

Synthesis Example 3
Synthesis of 5,8-bis(phenylamino)dinaphtho(2':3'-3:4)(2":3"-9:10)pyrene Dinaphtho(2':3'-3:4)(2":3"-9:10)pyrene is dissolved in carbon tetrachloride. While the resultant mixture is being cooled, 1 mol equivalent of bromine is added thereto. The mixture is reacted for 4 hours and brominated. Thereafter, the mixture is purified in accordance with a usual method, and 5,8-dibromodinaphtho(2':3'-3:4)(2":3"-9:10)pyrene is obtained. Phenylamine, potassium carbonate, and copper powder are added to the 5,8-dibromodinaphtho(2':3'-3:4)(2":3"-9:10)pyrene obtained in this way, and the mixture is reacted for 30 hours at 200° C. After the reaction solution is diluted with water, the reactant is eluted with chloroform. Thereafter, the resultant substance is purified in accordance with a usual method, and the 5,8-bis(phenylamino)dinaphtho pyrene expressed by the following formula is synthesized. (Note that, in the formula, "Ph" represents a phenyl group.)

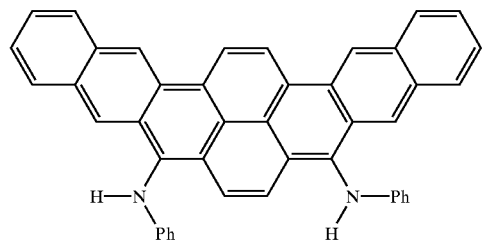

Synthesis Example 4
Synthesis of 5,8-bis(diphenylamino)dinaphtho(2':3'-3:4)(2":3"-9:10)pyrene Dinaphthopyrene is dissolved in carbon tetrachloride. While the resultant mixture is being cooled, 1 mol equivalent of bromine is added thereto. The mixture is reacted for 4 hours and brominated. Thereafter, the mixture is purified in accordance with a usual method, and 5,8-dibromodinaphthopyrene is obtained. Diphenylamine, potassium carbonate, and copper powder are added to the 5,8-dibromodinaphtho(2':3'-3:4)(2":3"-9:10)pyrene obtained in this way, and the mixture is reacted for 30 hours at 200° C. After the reaction solution is diluted with water, the reactant is eluted with chloroform. Thereafter, the resultant substance is purified in accordance with a usual method, and the 5,8-bis(diphenylamino)dinaphtho(2':3'-3:4)(2":3"-9:10)pyrene expressed by the following formula is synthesized. (Note that, in the formula, "Ph" represents a phenyl group.)

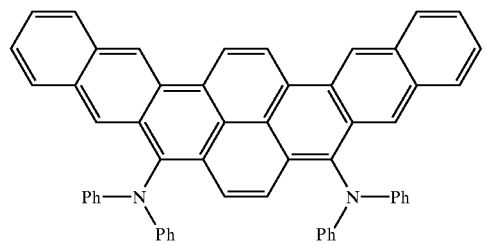

Example 1
A laminated-type organic EL element using dinaphtho(2':3'-3:4)(2":3"-9:10)pyrene in the light-emitting layer is prepared as follows. Namely, a glass substrate, on which ITO electrodes are formed as positive electrodes, is washed with water, acetone and isopropyl alcohol. Using a vacuum vapor deposition device (degree of vacuum=1×10$^{-6}$ Torr (1.3×10$^{-4}$ Pa), substrate temperature=room temperature), TPD serving as a positive hole transporting layer is covered on the ITO electrodes so as to be a thickness of 50 nm. Next, a light-emitting layer having a thickness of 20 nm is formed simultaneously by vapor depositing, on the positive hole transporting layer formed by the TPD, dinaphtho(2':3'-3:4)(2":3"-9:10)pyrene and CBP such that the CBP is 99 molecules (99 mol) to 1 molecule (1 mol) of the dinaphtho(2':3'-3:4)(2":3"-9:10)pyrene. Then, Alq serving as an electron transporting layer is covered so as to be a thickness of 30 nm on the light-emitting layer. Then, an Al—Li alloy (Li content=0.5% by mass) serving as the negative electrodes is vapor deposited so as to be a thickness of 50 nm on the electron transporting layer formed by the Alq. The organic EL element is thus prepared.

When voltage is applied to the ITO electrodes (positive electrodes) and the Al—Li alloy (negative electrodes) of the prepared organic EL element, the emission of green light at a voltage of 5V or more is observed in the organic EL element. At an applied voltage of 10V, the emission of green light, whose light-emitting luminance is 1200 cd/m² and whose peak is a wavelength of 500 nm, is observed.

Example 2

An organic EL element is prepared in the same way as in Example 1, except that the dinaphtho(2':3'-3:4)(2":3"-9:10) pyrene in Example 1 is replaced with 5,8-diphenyl-dinaphtho(2':3'-3:4)(2":3"-9:10)pyrene.

When voltage is applied to the ITO electrodes (positive electrodes) and the Al—Li alloy (negative electrodes) of the prepared organic EL element, the emission of green light at a voltage of 5V or more is observed in the organic EL element. At an applied voltage of 10V, the emission of green light, whose light-emitting luminance is 1850 cd/m² and whose peak is a wavelength of 510 nm, is observed.

Example 3

An organic EL element is prepared in the same way as in Example 1, except that the dinaphtho(2':3'-3:4)(2":3"-9:10) pyrene in Example 1 is replaced with 5,8-bis(phenylamino) dinaphtho (2':3'-3:4) (2":3"-9:10)pyrene.

When voltage is applied to the ITO electrodes (positive electrodes) and the Al—Li alloy (negative electrodes) of the prepared organic EL element, the emission of green light at a voltage of 5V or more is observed in the organic EL element. At an applied voltage of 10V, the emission of green light, whose light-emitting luminance is 1700 cd/m² and whose peak is a wavelength of 525 nm, is observed.

Example 4

An organic EL element is prepared in the same way as in Example 1, except that the CBP is not used and that dinaphtho(2':3'-3:4)(2":3"-9:10)pyrene in Example 1 is replaced with 5,8-bis(diphenylamino)dinaphtho (2':3'-3:4)(2":3"-9:10)pyrene.

When voltage is applied to the ITO electrodes (positive electrodes) and the Al—Li alloy (negative electrodes) of the prepared organic EL element, the emission of green light at a voltage of 6V or more is observed in the organic EL element. At an applied voltage of 10V, the emission of green light, whose light-emitting luminance is 1070 cd/m² and whose peak is a wavelength of 530 nm, is observed.

Example 5

An organic EL element is prepared in the same way as in Example 1, except that the dinaphtho(2':3'-3:4)(2":3"-9:10) pyrene in Example 1 is replaced with 5,8-diphenyl-dinaphtho(2':3'-3:4)(2":3"-9:10)pyrene.

When voltage is applied to the ITO electrodes (positive electrodes) and the Al—Li alloy (negative electrodes) of the prepared organic EL element, the emission of green light at a voltage of 5V or more is observed in the organic EL element. At an applied voltage of 10V, the emission of green light, whose light-emitting luminance is 1300 cd/m² and whose peak is a wavelength of 530 nm, is observed.

Example 6

An organic EL element is prepared in the same way as in Example 1, except that the positive hole transportation layer was not formed and instead it was replaced by positive hole transporting and light-emitting layer having thickness of 50 nm, and that the dinaphtho(2':3'-3:4)(2":3"-9:10)pyrene in Example 1 is replaced with 5,8-bis(diphenylamino) dinaphtho(2':3'-3:4)(2":3"-9:10)pyrene.

When voltage is applied to the ITO electrodes (positive electrodes) and the Al—Li alloy (negative electrodes) of the prepared organic EL element, the emission of green light at a voltage of 6V or more is observed in the organic EL element. At an applied voltage of 10V, the emission of green light, whose light-emitting luminance is 800 cd/m² and whose peak is a wavelength of 530 nm, is observed.

Example 7

An organic EL element is prepared in the same way as in Example 1, except that the dinaphtho(2':3'-3:4)(2":3"-9:10) pyrene in Example 1 is replaced with 5,8-bis (diphenylamino)dinaphtho(2':3'-3:4)(2":3"-9:10)pyrene, and the positive hole transporting layer is not formed, and the light-emitting layer is made to be a positive hole transporting and light-emitting layer having a thickness of 30 nm.

When voltage is applied to the ITO electrodes (positive electrodes) and the Al—Li alloy (negative electrodes) of the prepared organic EL element, the emission of green light at a voltage of 7V or more is observed in the organic EL element. At an applied voltage of 10V, the emission of green light, whose light-emitting luminance is 620 cd/m² and whose peak is a wavelength of 510 nm, is observed.

In accordance with the present invention, there are provided a condensed eight-ring aromatic compound which overcomes the above-described drawbacks of the prior art and which has high color purity of green light and excellent light-emitting efficiency, light-emitting luminance and the like and which is suitable for an organic EL element, an organic EL element which uses the condensed eight-ring aromatic compound and has high color purity of green light and excellent light-emitting efficiency, light-emitting luminance and the like, and an organic EL display which is high-performance and utilizes the organic EL element.

What is claimed is:

1. A dinaphthopyrene compound expressed by the following structural formula

Structural Formula

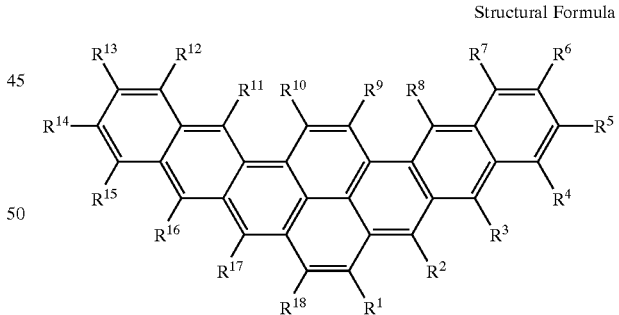

where $R^1$ through $R^{18}$ may be the same or may be different, and represent hydrogen atoms or substituents (excluding cases in which all are hydrogen atoms) and wherein the substituents are selected from halogen atoms, hydroxy groups, cyano groups, alkyl groups, alkoxy groups, aryl groups, aryloxy groups, arylamino groups, and diarylamino groups.

2. A dinaphthopyrene compound according to claim 1, wherein at least one of $R^1$ through $R^{18}$ is an aryl group.

3. A dinaphthopyrene compound according to claim 1, wherein at least one of $R^1$ through $R^{18}$ is selected from arylamino groups and diarylamino groups.

4. A dinaphthopyrene compound according to claim 1, wherein $R^1$, $R^3$ through $R^{16}$ and $R^{18}$ are hydrogen atoms and $R^2$ and $R^{17}$ are selected from phenyl groups, phenylamino groups, and diphenylamino groups.

5. A dinaphthopyrene compound according to claim 1, wherein $R^2$ and $R^{17}$ are the same.

6. A dinaphthopyrene compound according to claim 1, wherein the dinaphthopyrene compound is adapted for use with an organic EL element.

7. A dinaphthopyrene compound according to claim 2, wherein the dinaphthopyrene compound is adapted for use with at least one of an electron transporting layer and a light-emitting layer of an organic EL element.

8. A dinaphthopyrene compound according to claim 3, wherein the dinaphthopyrene compound is adapted for use with at least one of a positive hole transporting layer and a light-emitting layer of an organic EL element.

9. An organic EL element comprising an organic thin-film layer including a light-emitting layer in between a positive electrode and a negative electrode, and the organic thin-film layer contains a dinaphthopyrene compound, wherein the dinaphthopyrene compound is expressed by the following structural formula

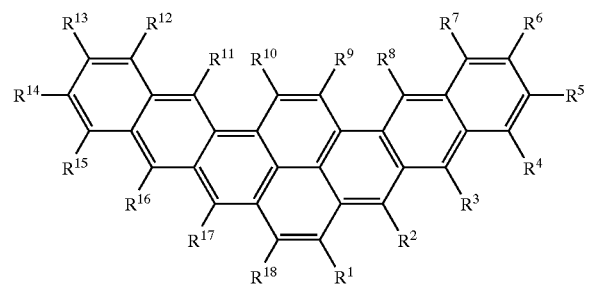

where $R^1$ through $R^{18}$ may be the same or may be different, and represent hydrogen atoms or substituents (excluding cases in which all are hydrogen atoms) and wherein the substituents are selected from halogen atoms, hydroxy groups, cyano groups, alkyl groups, alkoxy groups, aryl groups, aryloxy groups, arylamino groups, and diarylamino groups.

10. An organic EL element according to claim 9, wherein the light-emitting layer comprises the dinaphthopyrene compound.

11. An organic EL element according to claim 9, wherein at least one of $R^1$ through $R^{18}$ is an aryl group.

12. An organic EL element according to claim 9, wherein at least one of $R^1$ through $R^{18}$ is an arylamino group.

13. An organic EL element according to claim 12, wherein the arylamino group is expressed by the following structural formula

where $Ar^1$ represents an aryl group and $R^{19}$ represents a hydrogen atom, or a straight chain, branched or cyclic alkyl group having from 1 to 10 carbon atoms.

14. An organic EL element according to claim 9, wherein at least one of $R^1$ through $R^{18}$ is a diarylamino group.

15. An organic EL element according to claim 14, wherein the diarylamino group is expressed by the following structural formula

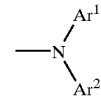

where $Ar^1$ and $Ar^2$ may be the same or different, and each represents an aryl group.

16. An organic EL element according to claim 9, wherein the organic thin-film layer has an electron transporting layer, and the electron transporting layer comprises the dinaphthopyrene compound.

17. An organic EL element according to claim 16, wherein at least one of $R^1$ through $R^{18}$ in the dinaphthopyrene compound contained in the electron transporting layer is an aryl group.

18. An organic EL element according to claim 9, wherein the organic thin-film layer has a positive hole transporting layer, and the positive hole transporting layer comprises the dinaphthopyrene compound.

19. An organic EL element according to claim 18, wherein at least one of $R^1$ through $R^{18}$ in the dinaphthopyrene compound contained in the positive hole transporting layer is selected from arylamino groups and diarylamino groups.

20. An organic EL element according to claim 9, wherein in the dinaphthopyrene compound, the $R^1$, $R^3$ through $R^{16}$, and $R^{18}$ are hydrogen atoms and $R^2$ and $R^{17}$ are selected from phenyl groups, phenylamino groups, and diphenylamino groups.

21. An organic EL element according to claim 9, wherein $R^2$ and $R^{17}$ are the same.

22. An organic EL element according to claim 9, wherein the light-emitting layer contains a host compound whose light absorption wavelength is at a shorter wavelength side of a light absorption wavelength of the dinaphthopyrene compound, and whose light emitting wavelength is in a vicinity of the light absorption wavelength of the dinaphthopyrene compound.

23. An organic EL element according to claim 22, wherein a content of the host compound is 90 mol or more with respect to 1 mol of the dinaphthopyrene compound.

24. An organic EL element according to claim 22, wherein the host compound is a 4,4'-bis(9-carbazolyl)-biphenyl (CBP) expressed by the following structural formula

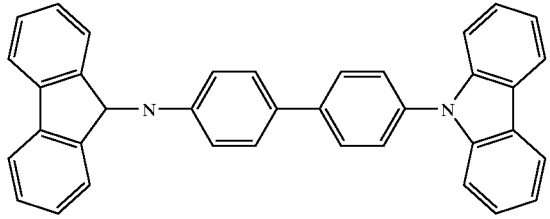

25. An organic EL element according to claim 9, wherein a thickness of the light-emitting layer is 5 to 50 nm.

26. An organic EL element according to claim 9, wherein an emission wavelength of the organic EL element is 490 to 560 nm.

27. An organic EL display comprising an organic EL element which comprises an organic thin-film layer including a light-emitting layer in between a positive electrode and a negative electrode, and the organic thin-film layer contains a dinaphthopyrene compound;

wherein the dinaphthopyrene compound is expressed by the following structural formula

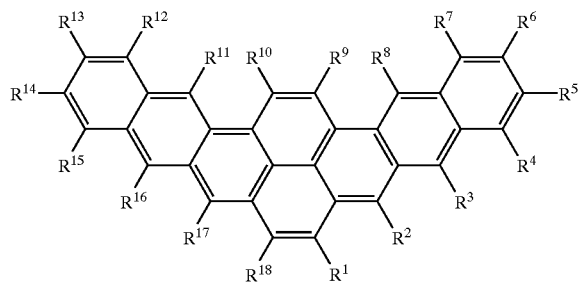

where $R^1$ through $R^{18}$ may be the same or may be different, and represent hydrogen atoms or substituents (excluding cases in which all are hydrogen atoms) and wherein the substituents are selected from halogen atoms, hydroxy groups, cyano groups, alkyl groups, alkoxy groups, aryl groups, aryloxy groups, arylamino groups, and diarylamino groups.

28. An organic EL display according to claim 27, wherein the organic EL display is one of a passive matrix panel and an active matrix panel, wherein the organic EL element emits green light.

* * * * *

UNITED STATES PATENT AND TRADEMARK OFFICE
CERTIFICATE OF CORRECTION

PATENT NO. : 6,783,872 B2
DATED : August 31, 2004
INVENTOR(S) : Wataru Sotoyama et al.

Page 1 of 1

It is certified that error appears in the above-identified patent and that said Letters Patent is hereby corrected as shown below:

<u>Title page,</u>
Item [54], Title, change "DINAPHTOPYRENE" to -- DINAPHTHOPYRENE --

Signed and Sealed this

Eighteenth Day of January, 2005

JON W. DUDAS
*Director of the United States Patent and Trademark Office*